US008765937B2

(12) United States Patent
Basta et al.

(10) Patent No.: US 8,765,937 B2
(45) Date of Patent: Jul. 1, 2014

(54) PROCESS FOR THE ULTRAPURIFICATION OF ALGINATES

(75) Inventors: Giuseppe Pietro Pio Basta, Perugia (IT); Riccardo Calafiore, Perugia (IT)

(73) Assignee: GH Care, Inc., Dix Hills, NY (US)

( * ) Notice: Subject to any disclaimer, the term of this patent is extended or adjusted under 35 U.S.C. 154(b) by 145 days.

(21) Appl. No.: 12/863,912

(22) PCT Filed: Jan. 21, 2009

(86) PCT No.: PCT/IB2009/050221
§ 371 (c)(1),
(2), (4) Date: Jul. 21, 2010

(87) PCT Pub. No.: WO2009/093184
PCT Pub. Date: Jul. 30, 2009

(65) Prior Publication Data
US 2010/0298262 A1   Nov. 25, 2010

(30) Foreign Application Priority Data

Jan. 23, 2008   (IT) .............................. RM2008A0037

(51) Int. Cl.
*C08B 37/04*   (2006.01)
*C07H 1/06*   (2006.01)

(52) U.S. Cl.
USPC .................. 536/127; 536/124; 536/3; 514/54

(58) Field of Classification Search
USPC .................. 536/127, 124, 3; 514/54
See application file for complete search history.

(56) References Cited

U.S. PATENT DOCUMENTS

| 4,683,092 A | 7/1987 | Tsang |
| 5,139,783 A * | 8/1992 | Handjani et al. .............. 424/401 |
| 5,266,326 A * | 11/1993 | Barry et al. ................... 424/423 |
| 6,451,772 B1 | 9/2002 | Bousman et al. |
| 6,569,999 B2 * | 5/2003 | Machida et al. .............. 530/427 |
| 2007/0225727 A1 * | 9/2007 | Matsuhisa et al. ............. 606/107 |
| 2009/0316119 A1 * | 12/2009 | Parekh et al. ................... 355/30 |

FOREIGN PATENT DOCUMENTS

| WO | WO9313136 | 7/1993 |
| WO | WO 9313136 A1 * | 7/1993 |
| WO | WO03016334 | 2/2003 |

OTHER PUBLICATIONS

Calafiore, R., et al. "Standard Technical Procedures for Microencapsulation of Human Islets for Graft Into Nonimmunosuppressed Patients With Type 1 Diabetes Mellitus" Transplantation Proceedings. vol. 38, No. 4. May 2006. pp. 1156-1157.
De Vos, P., et al. "Alginate-Based Microcapsules for Immunoisolation of Pancreatic Islets" Biomaterials 27, Elsevier Science Publishers. vol. 27, No. 32. Nov. 2006. pp. 5603-5617.
Dusseault, J., et al. "Evaluation of Alginate Purification Methods: Effect on Polyphenol, Endotoxin, and Protein Contamination" Journal of Biomedical Materials Research. vol. 76A, No. 2. Feb. 2006. pp. 243-251.
Office Action dated Feb. 28, 2014 for Russian Application No. 2010135753/13(050796).

* cited by examiner

*Primary Examiner* — Patrick Lewis
*Assistant Examiner* — Everett White
(74) *Attorney, Agent, or Firm* — Tutunjian & Bitetto, P.C.

(57) ABSTRACT

A process for the ultrapurification of alginates is provided. In particular, the process may be used for microencapsulation in human cell transplants.

9 Claims, No Drawings

PROCESS FOR THE ULTRAPURIFICATION OF ALGINATES

TECHNICAL FIELD

The present invention relates to a process for the ultrapurification of alginates, in particular intended for microencapsulation in human cell transplants. The process is advantageously applied to the purification of the starting powder of pharmaceutical grade sodium alginate, removing endotoxins and endogenous pyrogens, yet keeping unchanged the molecular structure of the product.

RELATED ART

Sodium alginate (AG) is a polysaccharide extracted from some seaweeds, in particular *Macrocystis pyrifera*, present above all along the western coasts of the Pacific, which finds wide use in various fields, biotechnology included. The biopolymer salts, whose purification is subject-matter of the present invention, are water-soluble polysaccharides that are either spontaneously exuded by, or are extracted from living vegetal organisms. In fact, alginates are salts of alginic acid, which shows a copolymer structure Dmannuronic acid (-M-), and -L-guluronic acid (-G-) units). These units form polymer or dimer blocks MM or GG that at times alternate in the molecular pattern. Alginates molecular arrangement and composition are determined primarily by the source from which they are obtained. For example, the most commonly used alginates derive from brown seaweeds, and in particular products deriving from *Macrocystis pyrifera* have an M/G ratio equal to 1.56:1, while those from *Laminaria Hyperborea* have an M/G ratio equal to 0.45. Monovalent salts (Na, K) of alginate are typically water soluble, unlike divalent salts (Ba, Ca) or polyvalent salts (Fe, Al) that are found in the form of gels or solids.

AG has been used for years in food and pharmaceutical industries for the production, respectively, of fruit jellies and excipients for some classes of drugs (e.g., antiacids, etc.). However, commercially available sodium alginate is not sufficiently purified for special applications, such as applications in human transplants, where strict and internationally recognized quality control criteria are required, e.g. the guidelines of the Ministry of Health or those of U.S. Pharmacopeia.

Alginate is commercially available both as raw extract to be purified and as partially purified solution. The chemical composition of alginate powder is described in terms of fractions ($F_G$ or $F_M$) and M/G ratio. The product AG KELTONE LVCR, for example, has an endotoxin level in the range from about 30,000 EU/g to about 60,000 EU/g that, as such, makes it unsuitable for parenteral applications requiring an endotoxin level of no more than 100 EU/g, though lower levels are preferable.

As a consequence of this, and before AG KELTONE LVCR may be used parenterally, the level of endotoxin must be drastically reduced.

For over 20 years, AG has been employed in the preparation of microcapsules containing hybridoma cells for the production of monoclonal antibodies (Damon Biotech, Inc.) as well as for protection of pancreatic islands (insulae) transplants from host rejection reaction (U.S. Pat. No. 4,683,092). The first microcapsular transplant protocols in diabetic rodents and higher mammals clearly highlighted purity of employed material to be fundamental for success of the transplant itself. The main contaminant, possibly responsible for microcapsular transplant failure, is represented by bacterial lipopolysaccharide endotoxins, pyrogenic materials present in the membrane of gram negative bacteria. Such substances are resistant to most sterilization systems (e.g., autoclave). Techniques such as gamma irradiation or dry heat sterilization are able to destroy endotoxins, but can damage the materials or products to be sterilized. Moreover, their generally low molecular weight (10-20 Kd) does not allow removal thereof by standard filtration processes. In any case, it should be taken into account the need to obtain a sterile, as well as endotoxin-free product, in order to avoid the risk of secondary contamination. Lastly, materials which are to be introduced parenterally in the human body must have an endotoxin content lower than 100 EU/g, though it would be preferable to have a level lower than 50 EU/g. In case of AG use for the preparation of microcapsules containing pancreatic islands, for transplant purposes, endotoxin presence may invalidate capsule-provided immunoprotection, fostering the onset of a serious inflammatory reaction.

The need to obtain an ultrapurified product (virtually "endotoxin-free") has fostered in the last years the development of some purification methods, which however are unable to meet all industrial and safety demands. Some purification methods envisaging the W use of ion exchange resins with or without addition of polymyxin-b or filtration on cellulose acetate filters and further membrane dializationhad the drawbacks of allowing no relevant reduction of endotoxin levels (about 70-80 E.U./g), being excessive in cost and not applicable to the production of bulk quantities of AG owing to a remarkable loss of mass of the starting product, virtually indispensable to the start of protocols for clinical use, and, in the case of chloroform use, of exhibiting a difficult removal of said solvent, potentially toxic even in modest amounts. For example, in the technique employing AG precipitation in ethanol and subsequent extraction with chloroform, in order to obtain 1 liter of end product it is necessary to start from about 10 liters of AG. Moreover, a low yield of the product implies that different AG batches may have non-homogeneous features, certainly unsuitable for preparing products to be used in clinical protocols, for which technologies reproducible on a large scale are essential.

U.S. Pat. No. 6,451,772, starting from raw alginate, substantially provides filtration (and/or use of ion exchange resins) on polypropylene filters and subsequent filtrate precipitation with organic solvents. Main limitations of this process are represented by 1. the excessive cost of the materials, with respect to the end volumetric yield in terms of alginate produced, yield which however remains unsatisfactory,
2. the fact that the described methodology has excessive variability and does not allow the systematic availability of the product itself, though occasionally alginate with a sufficiently low endotoxin content is obtained; and
3. the modification effect on alginate structure caused by solvent use.

SUMMARY

It was now surprisingly found that replacing the precipitation operation with a filtration on a cartridge with charge-modified filtration membrane allows to obtain AG 1. of very high and constant purity degree (endotoxin content ≤20 EU/g)
2. ultrapurified on a large scale,
3. obtained without use of solvent, and therefore
   a. without modification of the chemical structure of alginate
   b. and without alginate contamination, so as to be accepted by protocols for parenteral use.

It is therefore subject-matter of the present invention a process for the obtainment of solutions of salts of alginate not structurally modified, with endotoxin content not higher than 20 EU/g, comprising the following steps:
   a. addition of commercial grade alginate powder to a saline solution, until obtaining an alginate solution having a concentration ranging from 1.6 to 2.0% by weight and pH adjustment in the range 7.4-7.6;
   b. filtration of the solution obtained from step a) on at least one hydrophilic filter and recovery of the solution obtained characterized in that the solution obtained from step b) is subjected to filtration on a hydrophobic filter and the obtained solution is recovered.

DETAILED DESCRIPTION OF PREFERRED EMBODIMENTS

According to the invention, an alginate used is sodium alginate having a composition comprising 52.26% M and 47.74% G, corresponding to an M/G ratio of 1.093. Advantageously, as alginate the product Keltone® LVCR was used.

The filtration of step b) preferably occurs by using three filters of cellulose acetate hydrophils, of which advantageously the first one has a pharmaceutical grade 30 and a nominal pore size of 2 μm, the second one a pharmaceutical grade 60 and a nominal pore size of 2 μm, and the third one a pharmaceutical grade 90 and a nominal pore size of 2 μm.

The second filtration makes use of a hydrophobic filter; it is advantageously preferred a charge-modified nylon filter, in particular a nylon 66 filter having a positive electric charge.

According to the invention, from the pharmaceutical grade AG powder, after molar dilution and multiple filtration, an end product is obtained (both in the form of solution and powder) whose endotoxin content does not exceed 20 E.U./g, in full compliance with the above-stated quality control criteria. The end product of the present inventors, usually available in 1.8% (w/v) solution, appropriately stored in a light-protected environment and at a temperature of 4°-6° C., is stable over time for about 5 years with a virtually absent protein content (<0.4%—another U.S. FDA bioinvisibility standard).

The invention exploits the chemical structure of lipopolysaccharide endotoxins (LPS) consisting of two portions, one hydrophilic (polysaccharide) and one hydrophobic (lipid). According to the invention, at the end of the ultrafiltration process (positively charged) nylon filters were employed, able to selectively bind the (hydrophobic) lipid portion of endotoxins, retaining them without altering and/or damaging AG structure. Adding the fourth filter, besides obviating further manipulations, required according to the prior art, guarantees a reproducible and simple result. Moreover, the chemical structure of the product is not altered, an aspect that had been highlighted in the above-mentioned U.S. Patent. This is incontrovertibly demonstrated by NMR spectra of the product showing, both in the case of Deuterium and of Carbon, that there are no structural nor molecular variations, not even minimal ones, between the (unpurified) starting product and the (ultrapurified, clinical grade) end product.

The process according to the invention allows obtaining about 50% of the starting product, in comparison with the 10% that may be calculated as recovered amount with the other methodologies.

The process of the present invention is simple to carry out, with limited manual interventions, therefore less at risk of contamination than the previous known ones, as it entails only the assembly of the suitable filter in the sanitary container ("housing") and the connection to the pumping system, down to the collecting one. The entire methodology may easily be conducted under a class II laminar-flow biological hood. Protein content of these samples ranges from 0 to 0.016 mg/ml. These data were calculated on values obtained in 21 different filtration processes accomplished in 2 years, as shown in the following Table 1.

TABLE 1

Protein content in various samples obtained according to the process of the invention

| Purification (internal number) | Proteins (mq/ml) |
|---|---|
| 1 | 0.0072 |
| 2 | 0.0087 |
| 3 | 0.0179 |
| 4 | 0.0095 |
| 5 | 0.0116 |
| 6 | 0.0121 |
| 7 | 0.0077 |
| 8 | 0.0062 |
| 9 | 0.0098 |
| 10 | 0.0118 |
| 11 | 0.0125 |
| 12 | 0.0124 |
| 13 | 0.0138 |
| 14 | 0.0089 |
| 15 | 0.0120 |
| 16 | 0.0131 |
| 17 | 0.0088 |
| 18 | 0.0063 |
| 19 | 0.0110 |
| 20 | 0.0157 |
| 21 | 0.0079 |

Average: 0.090846

The process of the invention comprises two steps:
1. Dissolving the AG powder in sodium chloride, controlling the pH, and passing through three hydrophilic filters.
   Preferably, as hydrophilic filtering material it is employed cellulose acetate, or other commercially available filters, for example "zetaplus" grade Cuno filters having a pore size ranging from 1 microns to 0.1 microns, with a wide filtering surface such as that employed by the present inventors, which offers the advantage of reducing filtration pressure without altering the product and of removing cell fragments and the so-called "inert" microparticles. The product thus obtained is sterile, with an endotoxin content anyhow higher than 100 EU/g;
2. the second step, supporting its originality, is the removing of residual endotoxins by a hydrophobic nylon filter having a positive electric charge, in order to bind the negative portion of the lipopolysaccharide preventing precipitation on solvent or of other techniques, obtaining a product ready for various uses, having an endotoxin content always lower than 30 EU/g.

The present invention finds application in the field of transplantation biotechnologies, in particular in the production of AG microcapsules suitably coated with polyamino acids and diluted AG, which were demonstrated to immunoprotect transplants of islands from host immune system cells. For several years now the inventors have been studying the transplant of microencapsulated pancreatic islands for therapy of type 1 diabetes mellitus (insulin-dependent, or T1DM) and this research activity is amply documented by scientific publications, mostly international ones. Moreover, thanks to the purity and high biocompatibility of the materials employed, the present inventors have been authorized by the Italian Istituto Superiore di Sanità to operatively begin a phase I clinical study related to transplant of microencapsulated human pancreatic islands in patients with T1DM, not pharmacologically immunosuppressed. From results obtained hereto it emerges that the microcapsules obtainable according to the invention are highly biocompatible, and the effectiveness of their product has been assessed by various international research laboratories.

EXAMPLES

For the preparation of the solution of sodium alginate, ultrapure and having an endotoxin level no higher than 20 EU/g, the following materials are needed:
Pyrex beaker,
Pyrex graduated cylinders,
Magnetic stirrer,
Silicone tube HW 155 inner diameter 5, outer diameter 8,
Peristaltic pump,
Sterile pipettes,
Certified endotoxin-free sterile bottles,
30, 60 and 90 pharmaceutical grade cellulose acetate filters with filtration coadjuvant comprised of diatomite and perlite, 20" height and 12" diameter
Filters with charge-modified Nylon 66 filtration membrane, pore size 0.2 μm, 20" height and 8" diameter.
AISI316 stainless steel sanitary container for 20" filtration cartridge, 12" diameter.
AISI316 stainless steel sanitary container for 20" filtration cartridge, 8" diameter.

The methodology of preparation of the solution of sodium alginate, ultrapure and with an endotoxin level no higher than 20 EU/g provides the following steps:
Sterilization of "Housings", Filters and Material of Use Glass containers (graduated beaker, graduated cylinder, bottles, etc.), connecting silicone tubes, AISI316 stainless steel sanitary containers, referred to as "Housings", and any other material (magnetic anchors, glass rods, etc.) used during the procedure for the preparation of the alginate solution and during the filtration steps are treated for 24 h with an 1% etoxate solution (E-Toxa-Clean®, Catalog Number E9029, SigmaAldrich, Milan, Italy), then accurately washed with deionized water and lastly autoclaved at 120° C. for 1 h. The 30, 60 and 90 pharmaceutical grade cellulose filters, all with 0.2 μm pore size, and the cartridge with charge-modified Nylon 66 filtration membrane, 0.2 μm pore size, are autoclaved, separately from the Housing, at 120° C. for 1 h.
Preparation of 1.8% AG Solution AG (the sodium salt of alginic acid (E400)) used is Keltone® LVCR (Kelco) having a low degree of viscosity and provided in form of ultrapure powder by the producer: Monsanto-Kelco (20N Wacker Dr, Chicago Ill. USA). The chemical composition of alginate powder is described in terms of fractions (FG or FM) and MIG ratio, and the alginate used by the present inventors has an M percent of 52.26% and a G percent of 47.74% and the M/G ratio is 1.093, determined through NMR (Nuclear Magnetic Resonance) analysis. All the procedure for the preparation of the 1.8% alginate solution is carried out under a class II laminar-flow biological hood. After weighing, the alginate powder is placed in a beaker and physiological solution (0.9% NaCl) is added slowly, to avoid clotting (the physiological solution used is sterile, apyrogenic and specific for injectable preparations) under bland stirring attained by use of a magnetic stirrer and a magnetic anchor, until obtaining a homogeneous solution.

Filtration Systems (Housing) Assembly

At the moment of use, the suitable filter is inserted in the housing, all the procedure is carried out under biological hood, and said filter is closed and assembled on the specific support. Silicone tubes are fastened at the outlet and inlet of the housing. The tube at the inlet of the filtration apparatus is hooked to a peristaltic pump, whereas the free end is immersed in the beaker containing the alginate solution. The free end of the silicone tube at the outlet of the filtration system is placed in a sterile collection bottle.
Filtration The solution is subjected to 4 different filtration steps, which are all performed by using the "Housing" filtration system and without breaks.

The first step provides for the solution to be filtered through a capsule of 30 pharmaceutical grade cellulose fiber (nominal pore size 2 μm). By means of the peristaltic pump, the housing is filled with about 7 liters of product, and filtrate collection is started. Pump rate is set at very low values, such as to allow a greater interaction between material and filter, and in fact the pressure inside the housing is held in the neighborhood of values of 1.5 bar. The first fraction of the filtrate, roughly quantifiable in 2 liters, is discarded as rich in extractables. The remainder is collected in plastic bottles, sterile and certified for endotoxin absence.

The second filtration step provides for the use of a 60 pharmaceutical grade cellulose fiber capsule (nominal pore size 2 μm). The rate at which the pump is set is, in this case as well, such as to generate in the filtration system a pressure of 1.5 bar. Collection occurs in the same type of plastic bottles described above.

The third step on cellulose fiber capsule provides for the use of a 90 pharmaceutical grade capsule (nominal pore size 2 μm). The rate at which the pump is set is, in this case as well, such as to generate in the filtration system a pressure of 1.5 bar. Collection occurs in the same type of plastic bottles described above.

The fourth and last filtration step provides for a cartridge with a charge-modified Nylon 66 filtration membrane, pore size 0.2 μm. In this last case the pressure generated by the peristaltic pump is held in the neighborhood of 0.3-0.5 bar, by acting on the control of the rate of the pump itself. The filtrate is now collected in glass bottles pretreated for endotoxins and sterilized in autoclave at 120° C. for 1 h.
End Product Evaluation

Example 2

Aliquots of the obtained product are tested for: endotoxin presence, by taking a suitable aliquot and sending it to a company specialized in endotoxin dosage by Limulus method (Lonza Verviers, SPRL), for protein content by Bradford method, for pH value at +4° C. and at +20° C., using the micrometric method, and to confirm its chemical composition and the related monomer fractions by NMR analysis. Endotoxin content is found lower than 20 EU/g. Heavy metal presence and product sterility are assessed through standard protocols.

The present invention finds application in the field of transplantation biotechnologies. In particular, in the case of the present inventors, AG microcapsules suitably coated with polyamino acids and diluted AG were demonstrated to immunoprotect cells from the immune system of the receiver. For several years now the inventors have been studying in their laboratory the transplant of microencapsulated pancreatic islands for therapy of type 1 (insulin-dependent) diabetes mellitus and this research activity is amply documented by scientific publications, mainly international ones. Moreover, thanks to the purity and high biocompatibility of the materials employed, the present inventors have been authorized by the Istituto Superiore di Sanita to operatively begin a phase I clinical study related to transplant of microencapsulated human pancreatic islands in diabetic receivers, not pharmacologically immunosuppressed. From results obtained hereto, it emerges that the microcapsules of the present inventors are highly biocompatible, and the effectiveness of their product has been assessed in various international research laboratories.

Capsules and artificial extracellular matrices for growth and differentiation of various cellular strains STANDARD OPERATIVE PROCEDURE (SOP) for the preparation of alginate/polyornithine (AG/PLO) microcapsules using sodium alginate produced according to the present invention
Reagents
  sterile and apyrogenic physiological solution;
  1.2% $CaCl_2$ solution in distilled water;
  solution of 55 mM Na-citrate in distilled water;
  0.12% and 0.06% polyornithine solutions in physiological solution
  (the above-mentioned solutions are sterilized by filtration)
  1.6% NAG, obtained by the aforedisclosed filtration process;
  0.05% NAG, by 1:10 dilution of the preceding one in physiological solution.
Method
  Islands are washed with physiological solution to remove any protein present.
  Then, for each ml of pellet 0.5 ml of physiological solution and 10 ml of 1.6% NAG are added, bringing the suspension to homogeneity.
  The peristaltic pump is adjusted at 15 ml/min and the air flow at 5 l/min, initially letting physiological solution flow through the system.
  In a 250 ml beaker, containing 200 ml of 1.2% $CaCl_2$, there will be collected the alginate microdrops which, by gelling, will form the island-containing alginate microcapsules. The distance of the needle from the meniscus of the CaCl2 solution, equal to about 3 cm, assumes critical importance. Capsules are left S min in $CaCl_2$, then 100 ml of 1.2% $CaCl_2$ are replaced with physiological solution and left again for S min. Then, after repeated washings with physiological solution, the capsules are transferred into a 50 ml falcon. Then, the following reactants will be added in sequence, in an amount equal to twice the volume taken up by the capsules, removing each time what was previously added, stirring and carrying out between a reactant and the other suitable washings with physiological solution:
  0.12% polyornithine for 10 min;
  0.06% polyornithine for 5 min;
  0.1% NAG for 6 min;
  55 mM Na-citrate for 2 min.
  The repeated washings carry out a two-fold function, as they allow on the one hand the removal of reactants or cellular debris, and on the other hand the removal of most of the smaller capsules, empty or broken, which by being lighter in weight settle more slowly. Upon ending these treatments, the capsules will be resuspended in CMRL 1066 medium. Prior to implant the capsules are washed with physiological solution, in which they will be resuspended also at the moment of implant.

The invention claimed is:

1. A process for the obtainment of solutions of not structurally modified salts of alginate, with endotoxin content not higher than 20 EU/g, comprising the following steps:
   a. adding commercial grade alginate powder to a saline solution for obtaining an alginate solution having a concentration ranging from 1.6 to 2.0% by weight and pH adjustment in the range 7.4-7.6;
   b. filtering the alginate solution obtained from step a) on at least one hydrophilic filter and recovering a filtered alginate solution; and
   c. filtering the filtered alginate solution obtained from step b) on a charge-modified hydrophobic filter and recovering an alginate solution having an endotoxin content less than 20 EU/g.

2. The process according to claim 1, wherein said alginate powder is sodium alginate powder.

3. The process according to claim 1, wherein said alginate has a composition comprising 52.26% M and 47.74% G, corresponding to an M/G ratio of 1.093.

4. The process according to claim 1, wherein said step of filtering on at least one hydrophilic filter is carried out on three hydrophil filters of cellulose acetate hydrophils.

5. The process according to claim 4, wherein the first one of said three filters has a pharmaceutical grade 30 and a nominal pore size of 2 µm, the second one of said three filters has a pharmaceutical grade 60 and a nominal pore size of 2 µm and the third one of said three filters has a pharmaceutical grade 90 and a nominal pore size of 2 µm.

6. The process according to claim 1, wherein said hydrophobic filter is a charge-modified Nylon filter.

7. The process according to claim 6, wherein said hydrophobic filter is a Nylon 66 filter having a positive electric charge.

8. A process for the obtainment of solutions of not structurally modified salts of alginate, with endotoxin content not higher than 20 EU/g, consisting of the following steps:
   a. adding commercial grade alginate powder to a saline solution for obtaining an alginate solution having a concentration ranging from 1.6 to 2.0% by weight and pH adjustment in the range 7.4-7.6;
   b. filtering the alginate solution obtained from step a) on pharmaceutical grade 30 cellulose hydrophilic filter having a nominal pore size of 2 µm;
   c. filtering the alginate solution obtained from step b) on pharmaceutical grade 60 cellulose hydrophilic filter having a nominal pore size of 2 µm;
   d. filtering the alginate solution obtained from step c) on pharmaceutical grade 90 cellulose hydrophilic filter having a nominal pore size of 2 µm; and
   e. filtering the alginate solution obtained from step d) on a charge-modified hydrophobic filter for recovering an alginate solution having an endotoxin content less than 20 EU/g.

9. The process of claim 8, wherein said charge-modified hydrophobic filter comprises a Nylon 66 filter having a positive electric charge.

* * * * *